US006993172B2

(12) United States Patent
Connell et al.

(10) Patent No.: US 6,993,172 B2
(45) Date of Patent: Jan. 31, 2006

(54) METHOD AND SYSTEM FOR AUTOMATED OUTLYING FEATURE AND OUTLYING FEATURE BACKGROUND DETECTION DURING PROCESSING OF DATA SCANNED FROM A MOLECULAR ARRAY

(75) Inventors: Scott D. Connell, Saratoga, CA (US); Herbert F. Cattell, Mountain View, CA (US); Glenda C. Delenstarr, Belmont, CA (US); Nicholas M Sampas, San Jose, CA (US); Andreas N. Dorsel, Menlo Park, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 696 days.

(21) Appl. No.: 09/895,756

(22) Filed: Jun. 29, 2001

(65) Prior Publication Data

US 2003/0081819 A1 May 1, 2003

(51) Int. Cl.
*G06K 9/00* (2006.01)
(52) U.S. Cl. .................................................. 382/129
(58) Field of Classification Search ........ 382/128–131, 382/133, 209, 218; 435/4, 30, 34, 39, 287.2; 702/27–28, 30, 32
See application file for complete search history.

(56) References Cited

U.S. PATENT DOCUMENTS

| | | | | |
|---|---|---|---|---|
| 5,837,475 A | * | 11/1998 | Dorsel et al. ................. | 435/7.1 |
| 6,083,763 A | * | 7/2000 | Balch .......................... | 436/518 |
| 6,100,030 A | * | 8/2000 | McCasky Feazel et al. .... | 435/6 |
| 6,122,407 A | | 9/2000 | Peters | |
| 6,249,593 B1 | | 6/2001 | Chu et al. | |
| 6,341,182 B1 | * | 1/2002 | Fitzgerald et al. .......... | 382/273 |
| 6,344,316 B1 | | 2/2002 | Lockhart et al. | |
| 6,349,144 B1 | * | 2/2002 | Shams ........................ | 382/129 |
| 6,355,423 B1 | | 3/2002 | Rothberg et al. | |
| 6,516,276 B1 | * | 2/2003 | Ghandour et al. ............ | 702/27 |

FOREIGN PATENT DOCUMENTS

| | | |
|---|---|---|
| EP | 0 902 394 | 3/1999 |
| EP | 0 998 137 | 5/2000 |
| EP | 1 162 572 | 12/2001 |
| WO | WO 01/55967 | 8/2001 |

OTHER PUBLICATIONS

European Patent Office Communication dated Nov. 6, 2003, enclosure of European Search Report and Annex to the EP Search Report for counterpart EP Application 02 25 4524.

* cited by examiner

*Primary Examiner*—Daniel Miriam

(57) ABSTRACT

A method and system for employing pixel-based, signal-intensity data contained within areas of a scanned image of a molecular array corresponding to features and feature backgrounds in order to determine whether or not the features or feature backgrounds have non-uniform signal intensities and are thus outlier features and outlier feature backgrounds. A calculated, estimated variance for the signal intensities within a feature or feature background is compared to a maximum allowable variance calculated for the feature or feature background based on a signal intensity variance model. When the experimental variance is less than or equal to the maximum allowable variance, the feature or feature background is considered to have acceptable signal-intensity uniformity. Otherwise, the feature or feature background is flagged as an outlier feature or outlier feature background.

19 Claims, 8 Drawing Sheets

METHOD AND SYSTEM FOR AUTOMATED OUTLYING FEATURE AND OUTLYING FEATURE BACKGROUND DETECTION DURING PROCESSING OF DATA SCANNED FROM A MOLECULAR ARRAY

TECHNICAL FIELD

The present invention relates to the processing of data scanned from a molecular array and, in particular, to a method and system for automatically detecting outlying signals scanned from features and feature backgrounds based on an estimated scanned data variance calculated from the scanned data and on a maximum variance threshold calculated from the scanned data and from a model variance.

BACKGROUND OF THE INVENTION

The present invention is related to processing of data scanned from molecular arrays. Molecular array technologies have gained prominence in biological research and are likely to become important and widely used diagnostic tools in the healthcare industry. Currently, molecular-array techniques are most often used to determine the concentrations of particular nucleic-acid polymers in complex sample solutions. Molecular-array-based analytical techniques are not, however, restricted to analysis of nucleic acid solutions, but may be employed to analyze complex solutions of any type of molecule that can be optically or radiometrically scanned and that can bind with high specificity to complementary molecules synthesized within, or bound to, discrete features on the surface of a molecular array. Because molecular arrays are widely used for analysis of nucleic acid samples, the following background information on molecular arrays is introduced in the context of analysis of nucleic acid solutions following a brief background of nucleic acid chemistry.

Deoxyribonucleic acid ("DNA") and ribonucleic acid ("RNA") are linear polymers, each synthesized from four different types of subunit molecules. The subunit molecules for DNA include: (1) deoxy-adenosine, abbreviated "A," a purine nucleoside; (2) deoxy-thymidine, abbreviated "T," a pyrimidine nucleoside; (3) deoxy-cytosine, abbreviated "C," a pyrimidine nucleoside; and (4) deoxy-guanosine, abbreviated "G," a purine nucleoside. The subunit molecules for RNA include: (1) adenosine, abbreviated "A," a purine nucleoside; (2) uracil, abbreviated "U," a pyrimidine nucleoside; (3) cytosine, abbreviated "C," a pyrimidine nucleoside; and (4) guanosine, abbreviated "G," a purine nucleoside. FIG. 1 illustrates a short DNA polymer 100, called an oligomer, composed of the following subunits: (1) deoxy-adenosine 102; (2) deoxy-thymidine 104; (3) deoxy-cytosine 106; and (4) deoxy-guanosine 108. When phosphorylated, subunits of DNA and RNA molecules are called "nucleotides" and are linked together through phosphodiester bonds 110–115 to form DNA and RNA polymers. A linear DNA molecule, such as the oligomer shown in FIG. 1, has a 5' end 118 and a 3' end 120. A DNA polymer can be chemically characterized by writing, in sequence from the 5' end to the 3' end, the single letter abbreviations for the nucleotide subunits that together compose the DNA polymer. For example, the oligomer 100 shown in FIG. 1 can be chemically represented as "ATCG." A DNA nucleotide comprises a purine or pyrimidine base (e.g. adenine 122 of the deoxy-adenylate nucleotide 102), a deoxy-ribose sugar (e.g. deoxy-ribose 124 of the deoxy-adenylate nucleotide 102), and a phosphate group (e.g. phosphate 126) that links one nucleotide to another nucleotide in the DNA polymer. In RNA polymers, the nucleotides contain ribose sugars rather than deoxy-ribose sugars. In ribose, a hydroxyl group takes the place of the 2' hydrogen 128 in a DNA nucleotide. RNA polymers contain uridine nucleosides rather than the deoxy-thymidine nucleosides contained in DNA. The pyrimidine base uracil lacks a methyl group (130 in FIG. 1) contained in the pyrimidine base thymine of deoxy-thymidine.

The DNA polymers that contain the organization information for living organisms occur in the nuclei of cells in pairs, forming double-stranded DNA helixes. One polymer of the pair is laid out in a 5' to 3' direction, and the other polymer of the pair is laid out in a 3' to 5' direction. The two DNA polymers in a double-stranded DNA helix are therefore described as being anti-parallel. The two DNA polymers, or strands, within a double-stranded DNA helix are bound to each other through attractive forces including hydrophobic interactions between stacked purine and pyrimidine bases and hydrogen bonding between purine and pyrimidine bases, the attractive forces emphasized by conformational constraints of DNA polymers. Because of a number of chemical and topographic constraints, double-stranded DNA helices are most stable when deoxy-adenylate subunits of one strand hydrogen bond to deoxy-thymidylate subunits of the other strand, and deoxy-guanylate subunits of one strand hydrogen bond to corresponding deoxy-cytidilate subunits of the other strand.

FIGS. 2A–B illustrate the hydrogen bonding between the purine and pyrimidine bases of two anti-parallel DNA strands. FIG. 2A shows hydrogen bonding between adenine and thymine bases of corresponding adenosine and thymidine subunits, and FIG. 2B shows hydrogen bonding between guanine and cytosine bases of corresponding guanosine and cytosine subunits. Note that there are two hydrogen bonds 202 and 203 in the adenine/thymine base pair, and three hydrogen bonds 204–206 in the guanosine/cytosine base pair, as a result of which GC base pairs contribute greater thermodynamic stability to DNA duplexes than AT base pairs. AT and GC base pairs, illustrated in FIGS. 2A–B, are known as Watson-Crick ("WC") base pairs.

Two DNA strands linked together by hydrogen bonds forms the familiar helix structure of a double-stranded DNA helix. FIG. 3 illustrates a short section of a DNA double helix 300 comprising a first strand 302 and a second, anti-parallel strand 304. The ribbon-like strands in FIG. 3 represent the deoxyribose and phosphate backbones of the two anti-parallel strands, with hydrogen-bonding purine and pyrimidine base pairs, such as base pair 306, interconnecting the two strands. Deoxy-guanylate subunits of one strand are generally paired with deoxy-cytidilate subunits from the other strand, and deoxy-thymidilate subunits in one strand are generally paired with deoxy-adenylate subunits from the other strand. However, non-WC base pairings may occur within double-stranded DNA. Generally, purine/pyrimidine non-WC base pairings contribute little to the thermodynamic stability of a DNA duplex, but generally do not destabilize a duplex otherwise stabilized by WC base pairs. However, purine/purine base pairs may destabilize DNA duplexes.

Double-stranded DNA may be denatured, or converted into single stranded DNA, by changing the ionic strength of the solution containing the double-stranded DNA or by raising the temperature of the solution. Single-stranded DNA polymers may be renatured, or converted back into DNA duplexes, by reversing the denaturing conditions, for example by lowering the temperature of the solution containing complementary single-stranded DNA polymers. During renaturing or hybridization, complementary bases of anti-parallel DNA strands form WC base pairs in a cooperative fashion, leading to regions of DNA duplex. Strictly A-T and G-C complementarity between anti-parallel polymers leads to the greatest thermodynamic stability, but partial complementarity including non-WC base pairing may also occur to produce relatively stable associations between partially-complementary polymers. In general, the longer the regions of consecutive WC base pairing between two nucleic acid polymers, the greater the stability of hybridization between the two polymers under renaturing conditions.

The ability to denature and renature double-stranded DNA has led to development of many extremely powerful and discriminating assay technologies for identifying the presence of DNA and RNA polymers having particular base sequences or containing particular base subsequences within complex mixtures of different nucleic acid polymers, other biopolymers, and inorganic and organic chemical compounds. These methodologies include molecular-array-based hybridization assays. FIGS. 4–7 illustrate the principle of molecular-array-based hybridization assays. A molecular array (402 in FIG. 4) comprises a substrate upon which a regular pattern of features are prepared by various different types of manufacturing processes. The molecular array 402 in FIG. 4, and in subsequent FIGS. 5–7, has a grid-like two-dimensional array of square features, such as feature 404 shown in the upper left-hand corner of the molecular array. Each feature of the molecular array contains a large number of identical oligonucleotides covalently bound to the surface of the feature. In general, chemically distinct oligonucleotides are bound to the different features of a molecular array, so that each feature corresponds to a particular nucleotide sequence. In FIGS. 4–6, the principle of molecular-array-based hybridization assays is illustrated with respect to the single feature 404 to which a number of identical oligonucleotides 405–409 are bound. In practice, each feature of the molecular array contains an enormous number of oligonucleotide molecules, but, for the sake of clarity, FIGS. 4–6 only show a small number.

Once a molecular array has been prepared, the molecular array may be exposed to a sample solution of DNA molecules that includes DNA molecules (410–413 in FIG. 4) labeled with fluorophores, chemoluminescent compounds, or radioactive atoms 415–418. A labeled DNA molecule that contains a nucleotide sequence complementary to the base sequence of an oligonucleotide bound to the molecular array may hybridize through base pairing interactions to the oligonucleotide. FIG. 5 shows a number of labeled DNA molecules 502–504 hybridized to oligonucleotides 505–507 bound to the surface of the molecular array 402. DNA molecules that do not contains nucleotide sequences complementary to any of the oligonucleotides bound to the molecular array do not hybridize stably to oligonucleotides bound to the molecular array and generally remain in solution, such as labeled DNA molecules 508 and 509. The sample solution is then rinsed from the surface of the molecular array, washing away any unbound labeled DNA molecules. Finally, as shown in FIG. 6, the bound labeled DNA molecules are detected via optical or radiometric scanning. Optical scanning involves exciting labels of bound labeled DNA molecules with electromagnetic radiation of appropriate frequency and detecting fluorescent emissions from the labels, or detecting light emitted from chemoluminescent labels. When radioisotope labels are employed, radiometric scanning can be used to detect radiation emitted from labeled DNA molecules hybridized to oligonucleotides bound to the surface of the molecular array. Additional types of signals are also possible, including electrical signals generated by electrical properties of bound target molecules, magnetic properties of bound target molecules, and other such physical properties of bound target molecules that that can produce a detectable signal. Optical, radiometric, or other types of scanning produce an analog or digital representation of the molecular array as shown in FIG. 7, with features to which labeled DNA molecules are hybridized similar to 706 optically or digitally differentiated from those features to which no labeled DNA molecules are bound. In other words, the analog or digital representation of a scanned molecular array displays positive signals for features to which labeled DNA molecules are hybridized and displays negative features to which no, or an undetectably small number of, labeled DNA molecules are bound. Features displaying positive signals in the analog or digital representation indicate the presence of DNA molecules with complementary nucleotide sequences in the original sample solution. Moreover, the signal intensity produced by a feature is generally related to the amount of labeled DNA bound to the feature, in turn related to the concentration, in the sample to which the molecular array was exposed, of labeled DNA complementary to the oligonucleotide within the feature.

Molecular-array-based hybridization techniques allow extremely complex solutions of DNA molecules to be analyzed in a single experiment. Molecular arrays may contain hundreds, thousands, or tens of thousands or different oligonucleotides, allowing for the detection of hundreds, thousands, or tens of thousands of different DNA polymers containing complementary nucleotide sub-sequences in the complex DNA solutions to which the molecular array is exposed. In order to perform different sets of hybridization analyses, molecular arrays containing different sets of bound oligonucleotides are manufactured by any of a number of complex manufacturing techniques. These techniques generally involve synthesizing the oligonucleotides within corresponding features of the molecular array through complex iterative synthetic steps.

As pointed out above, molecular-array-based assays can involve other types of biopolymers, synthetic polymers, and other types of chemical entities. For example, one might attach protein antibodies to features of the molecular array that would bind to soluble labeled antigens in a sample solution. Many other types of chemical assays may be facilitated by molecular array technologies. For example, polysaccharides, glycoproteins, synthetic copolymers, including block coplyomers, biopolymer-like polymers with synthetic or derivitized monomers or monomer linkages, block copolymers, and many other types of chemical entities may serve as probe and target molecules for molecular-array-based analysis. A fundamental principle upon which molecular arrays are based is that of specific recognition, by probe molecules affixed to the molecular array, of target molecules, whether by sequence-mediated binding affinities, binding affinities based on conformational or topological properties of probe and target molecules, or binding affinities based on spatial distribution of electrical charge on the surfaces of target and probe molecules.

DNA, and other biological polymers, may be labeled with different chemical chromophores, radioactive nuclides, or other signal-generating entities, and may be optically scanned at different wavelengths of light, radiometrically scanned for different types of radioactive emission within different energy ranges, or scanned by other techniques appropriate to detect signals produced by other signal-generating entities. In the case of optical scanning, each different wavelength at which a molecular array is scanned produces a different signal. Thus, in optical scanning, it is common to describe the signal produced by scanning in terms of the color of the wavelength of light employed for the scan. For example, a red signal is produced by scanning a molecular array with light having a wavelength corresponding to that of visible red light.

Scanning of a feature by an optical scanning device or radiometric scanning device generally produces a scanned image comprising a rectilinear grid of pixels, with each pixel having a corresponding signal intensity. FIG. 8A shows a portion of a scanned image of a molecular array that includes a pixel-based image of a disk-shaped feature of a molecular array. In FIG. 8A, the feature corresponds to a disk-shaped region 802 of pixels having relatively high signal intensities. Surrounding the feature 802 is a ring-like region 804 of pixels with relatively low measured intensities. The portion of the scanned image shown in FIG. 8A is thus conceptually equivalent to a digital, black-and-white photograph of the feature taken with light within a narrow range of wavelengths. Generally, the location of the disk-shaped region 802 corresponding to a feature is determined by various scanned image-to-scanned-molecular-array alignment techniques and procedures.

It is desirable for the signal intensities, or counts, of pixels within the area of a pixel-based scanned image corresponding to a feature to be relatively uniform. Similarly, it is also desirable for the signal intensities within background regions surrounding features to be relatively uniform. Non-uniform signal intensity distributions generally indicate the occurrence of one or more error or noise conditions that may prevent meaningful data from being collected from the feature.

Figures 8A, 8B:
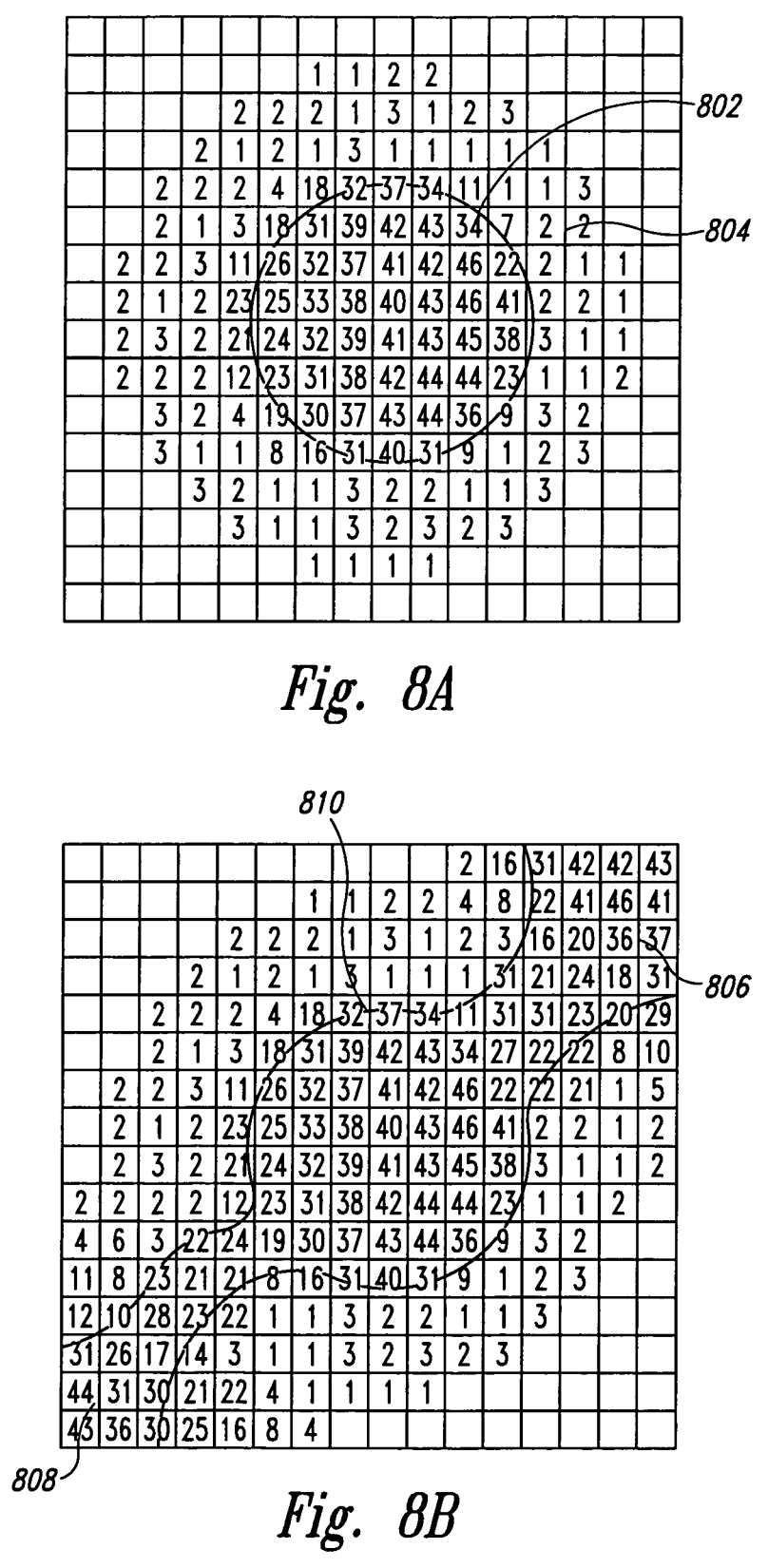
Figures 8C, 8D:
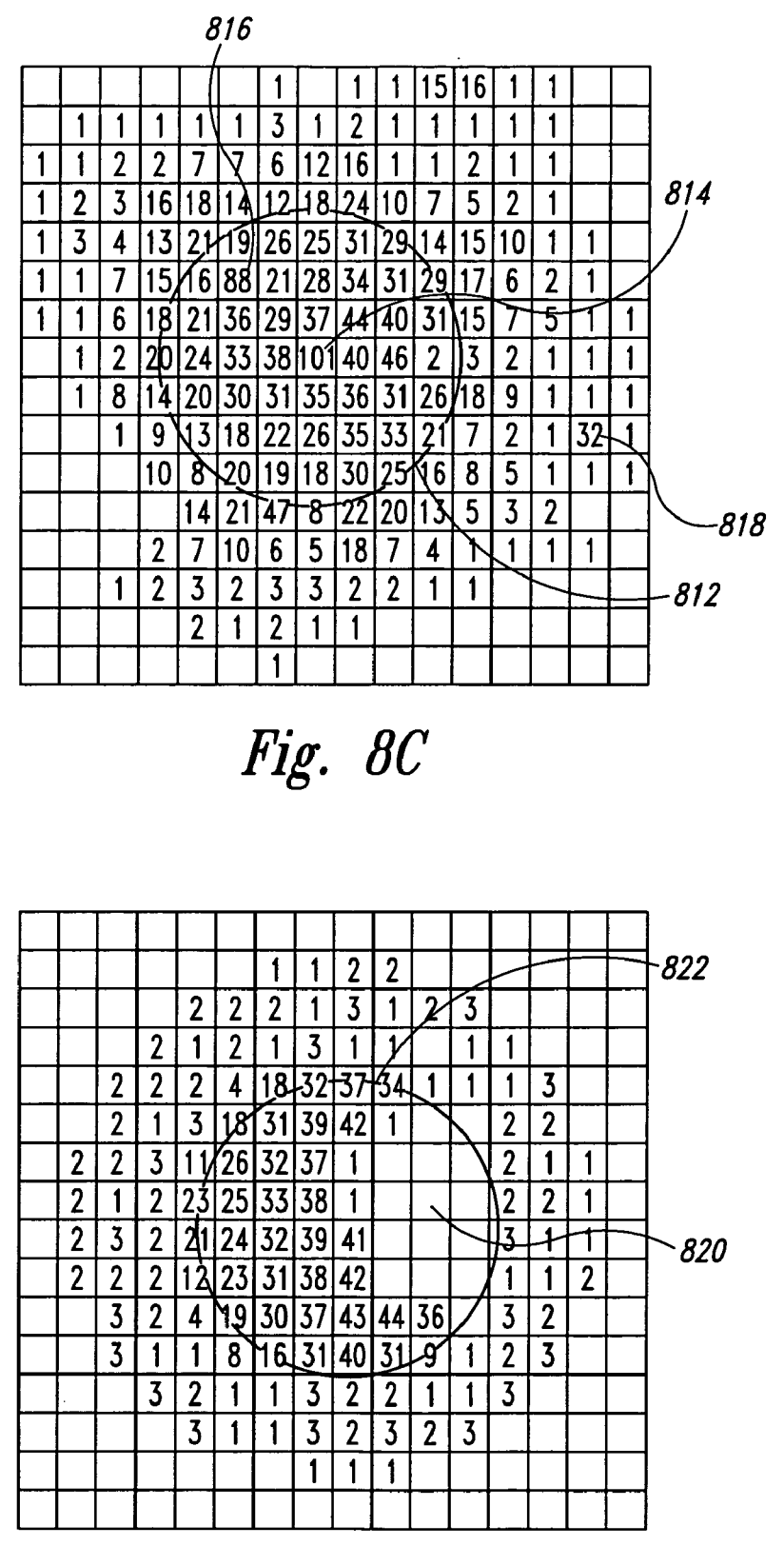

FIGS. 8B–D illustrate various non-uniform signal intensity distributions within a scanned image of a molecular array feature. In FIG. 8B, for example, relatively large signal intensities are seen in regions 806 and 808 at the upper right, and lower left, of the scanned image as well as within the disk-shaped area 810 corresponding to a feature. Such non-uniform distribution of signal intensities may indicate defects in the preparation of the molecular array, including defects in the synthesis of probe molecules bound to the molecular array, contamination of the surface of the molecular array with a chromophore that responds to impinging light in a similar fashion to the response by the chromophore with which target molecules are labeled, flaws in the scanning device, or other such defects. In FIG. 8C, the signal intensities within the feature 812 are relatively uniform, with the exception of a number of extremely high, outlying signal intensities in individual pixels, such as pixels 814, 816, and 818. Such outlying pixel intensities may represent scanner measurement errors or defects in digital processing and digital representation of the scanned data. In FIG. 8D, a relatively large area 820 within a feature 822 has produced no signal, and therefore represents a significant spatial non-uniformity of pixel intensities. A condition such as that shown in FIG. 8D may arise when probe molecules are not uniformly bound to the surface of the molecular array within a feature, because of overlying contamination that masks the signal, or for other reasons. In the situations illustrated in FIGS. 8B–D, the sum of the pixel intensities within the disk-shaped region of the optical image corresponding to a feature may produce a total signal intensity, or count, for the feature that does not reflect the theoretical count that would be produced by scanning the feature were the one or more error conditions or noise conditions not present. Such scanned features suffering from non-uniform pixel intensities need to be recognized during processing of data scanned from a molecular array and flagged as outlier features, to prevent reporting of flawed and erroneous experimental results.

Currently, outlier features, or feature backgrounds, are commonly identified by using negative control features manufactured into molecular arrays and by manual inspection of scanned images. However, control-feature-based outlier detection may be insensitive to various types of non-uniformities and significantly adds to the cost of molecular array manufacture and molecular array scanning and data processing. Manual outlier detection suffers from the inaccuracies and deficiencies well-known to occur in most human-dependent tasks, and is also quite slow and economically inefficient. Thus, designers, manufacturers, and users of molecular arrays have recognized the need for a more accurate, automated technique for recognizing outlier features and outlier feature backgrounds in scanned images of molecular arrays.

SUMMARY OF THE INVENTION

The present invention is directed towards a method and system for identifying outlier features and outlier feature backgrounds in scanned images of molecular arrays. The method and system of the present invention employ pixel-based, signal-intensity data contained within areas of a scanned image of a molecular array corresponding to features and feature backgrounds in order to determine whether or not the features or feature backgrounds have non-uniform signal intensities and are thus outlier features and outlier feature backgrounds. A calculated, estimated variance for the signal intensities within a feature or feature background is compared to a maximum allowable variance calculated for the feature or feature background based on a signal intensity variance model. When the experimental variance is less than or equal to the maximum allowable variance, the feature or feature background is considered to have acceptable signal-intensity uniformity. Otherwise, the feature or feature background is flagged as an outlier feature or outlier feature background.

BRIEF DESCRIPTION OF THE DRAWINGS

FIG. 8A shows a pixel-based result from scanning a disk-shaped feature of a molecular array.

FIGS. 8B–D illustrate various non-uniform signal intensity distributions within a scanned optical image of a molecular array feature.

DETAILED DESCRIPTION OF THE INVENTION

Figure 1:
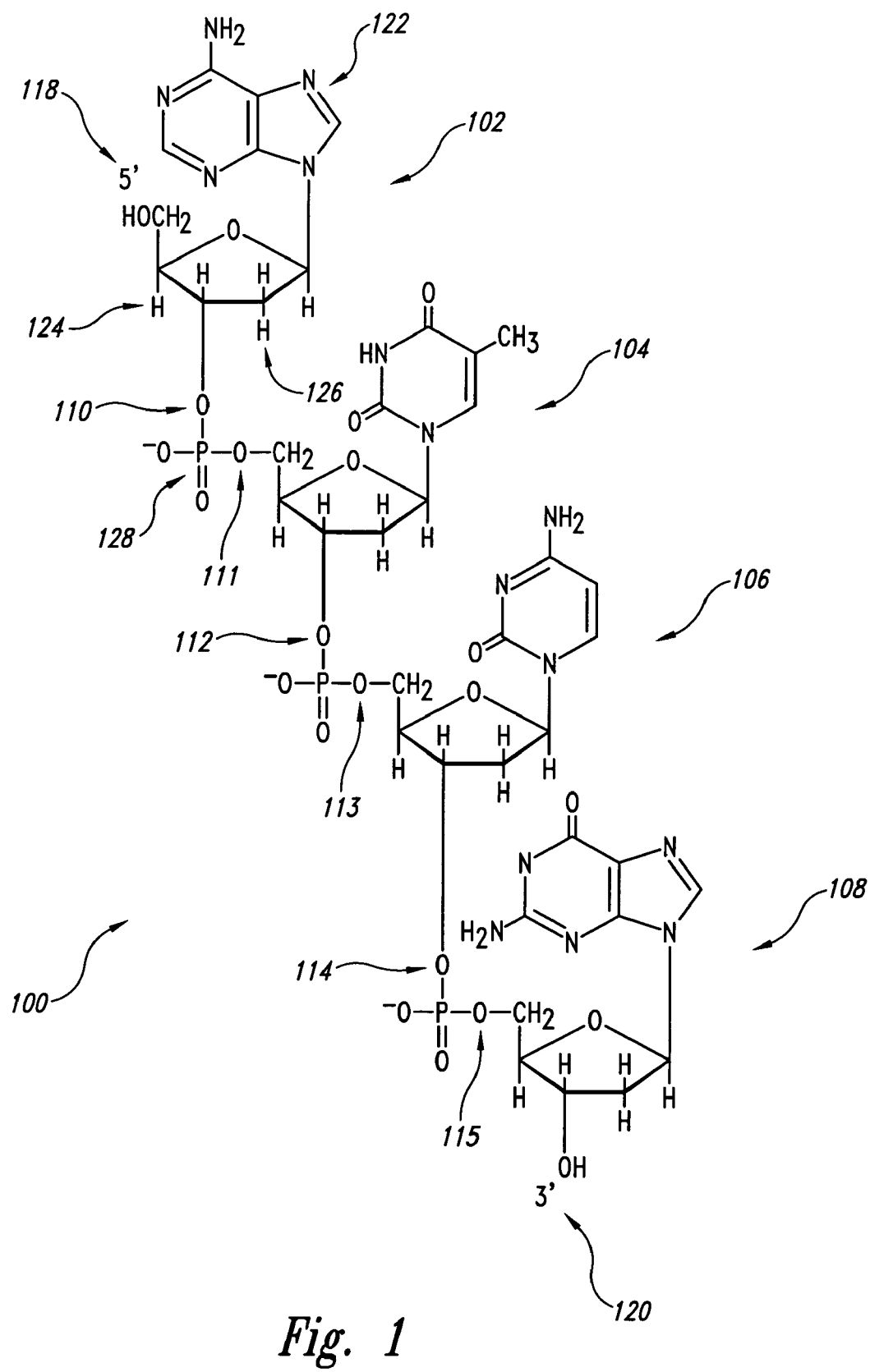
FIG. 1 shows a linear DNA polymer.
Figure 2A:
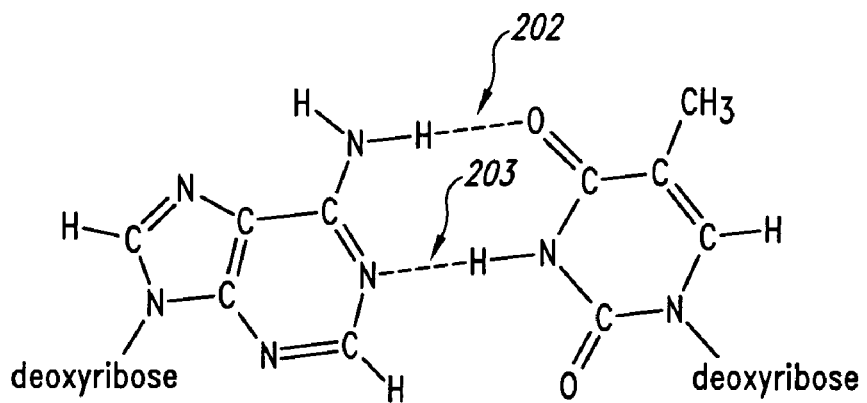
FIGS. 2A–B illustrate the hydrogen bonding between purine/pyrimidine bases of two anti-parallel DNA strands.
Figure 2B:
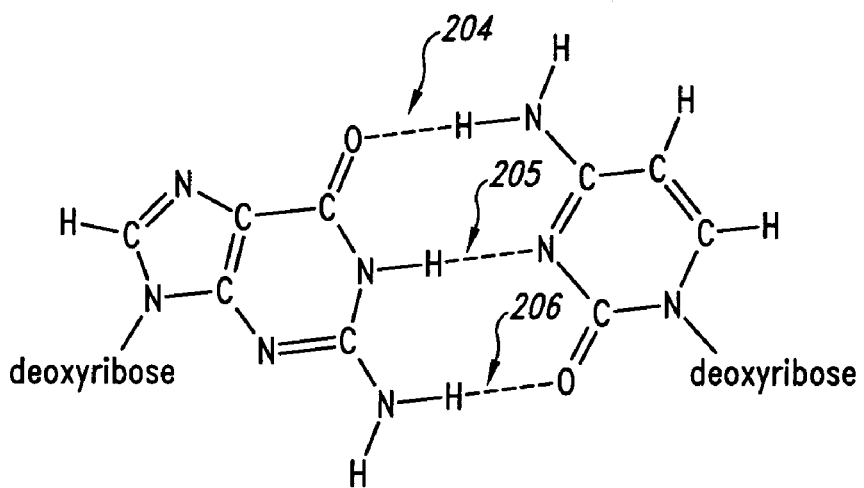
Figure 3:
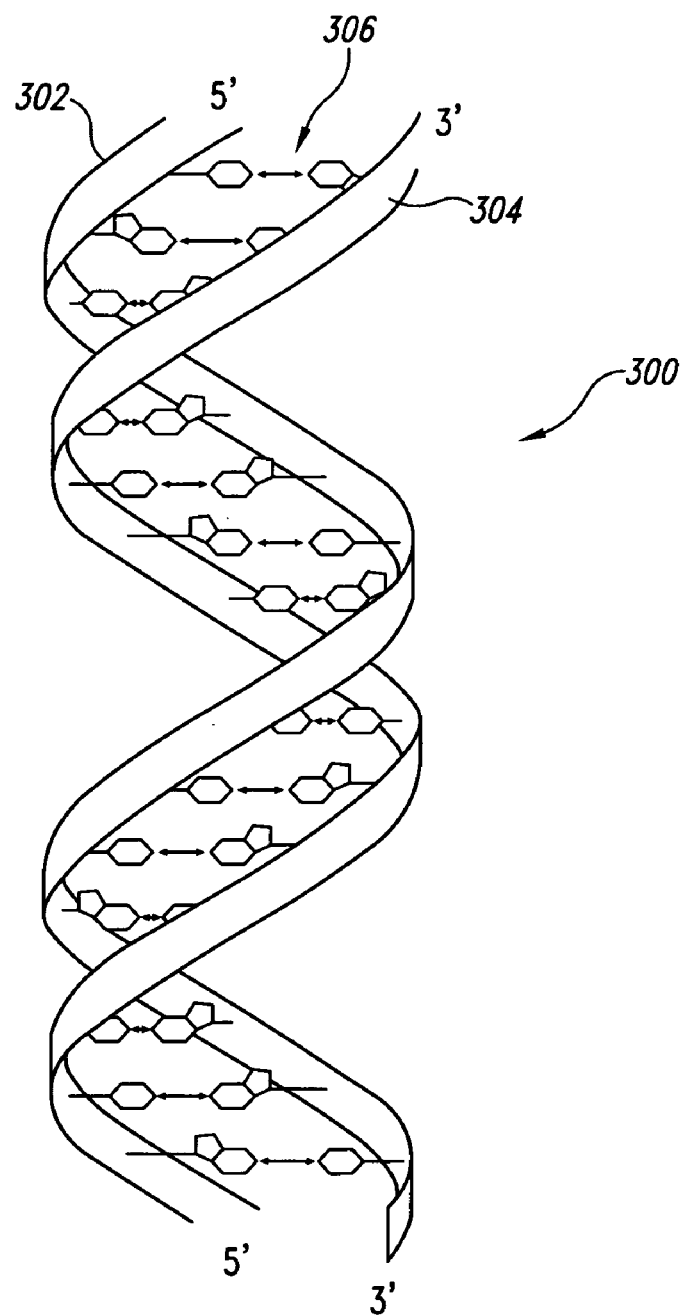
FIG. 3 illustrates a short section of a DNA double helix.
Figure 4:
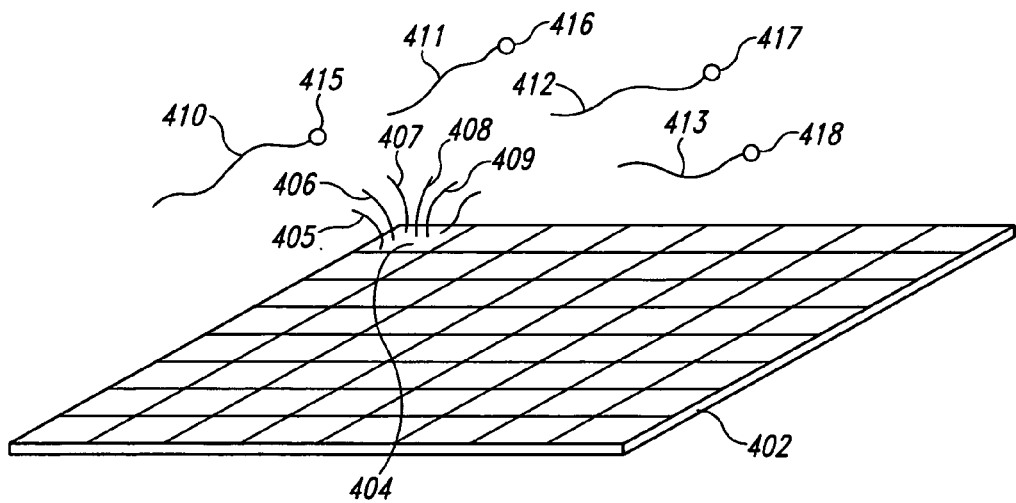
FIGS. 4–7 illustrate the principle of molecular-array-based hybridization assays.
Figure 5:
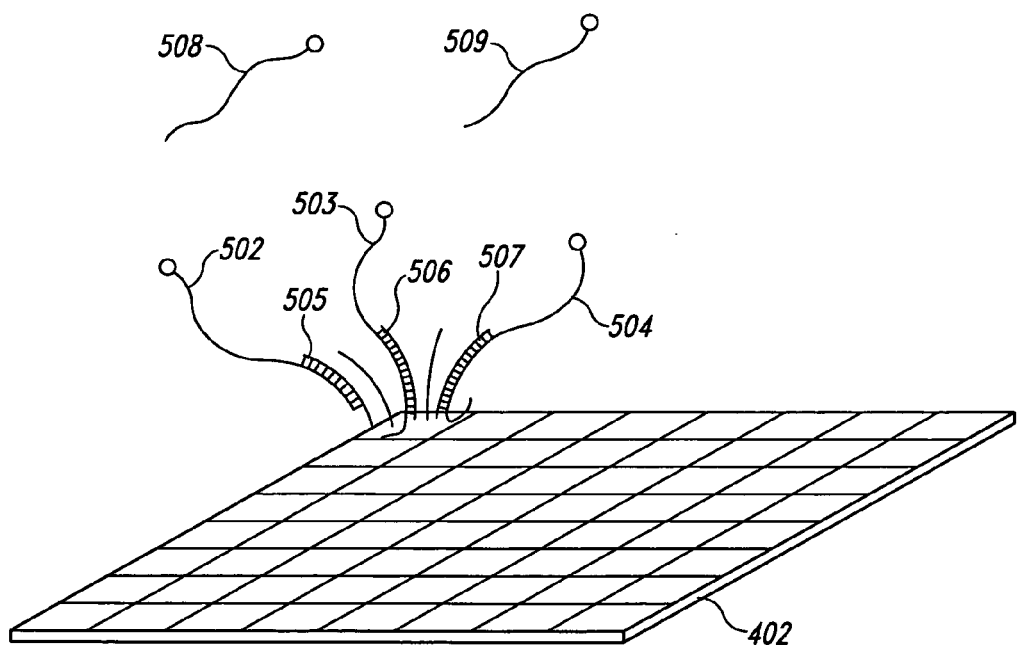
Figure 6:
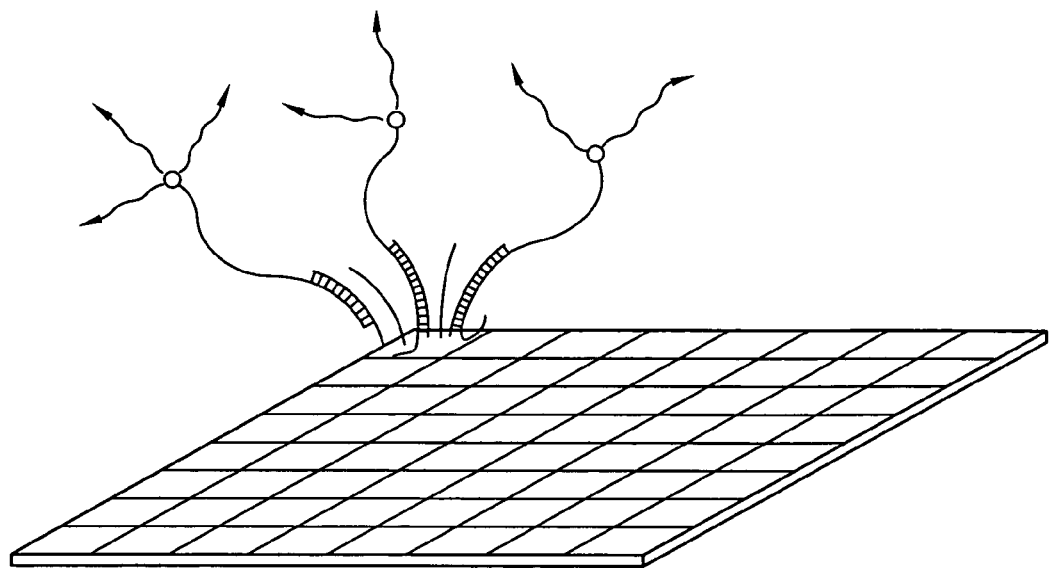
Figure 7:
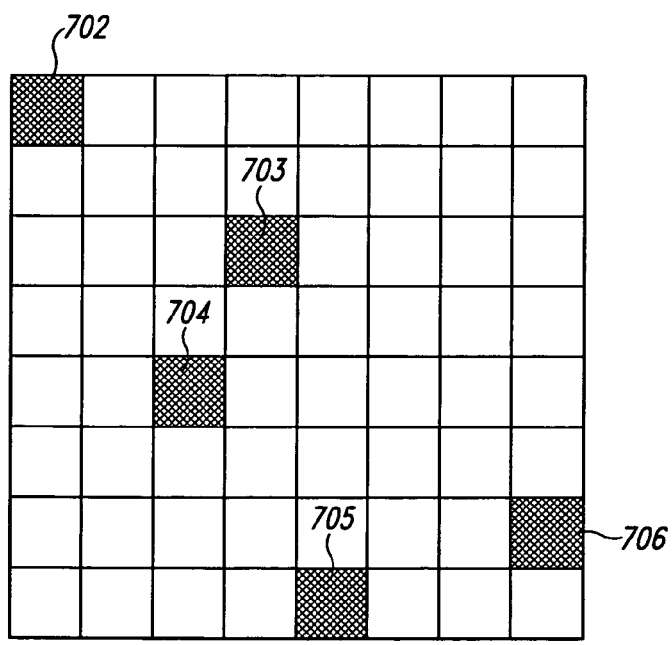

The present invention is directed to identifying outlier features and outlier feature backgrounds within scanned images of molecular arrays. The variance of signal intensities within a feature or feature background is compared to a maximum allowable variance calculated based on a variance model in order to determine whether or not the region of a scanned image of a molecular array corresponding to a feature or feature background contains adequately uniform pixel-based signal intensities within. In the following, a description of the variance model and the fundamental statistical concepts and distributions on which it is based is provided with reference to FIGS. 9A–C and a number of mathematical formulas. Following this discussion, a C++-like pseudocode implementation of automated outlier detection functionality that may be embedded within a molecular-array data processing system is provided as a described embodiment of the present invention.

Data processing techniques employed in outlier detection involve application of various statistical measurements on the per-pixel counts, or pixel-based signal intensities measured for a particular feature or feature background and included in a digital representation of the scanned image of the molecular array. A molecular array scanner produces a raw digital representation including a count, or signal intensity, for each pixel within the digital representation. As a first step in processing the raw data, net signals "$s_{net}$" are calculated from measured signals "$s_{measured}$" via a subtractive process:

$$s_{net} = s_{measured} - s_{offset}$$

For each measured per-pixel count, or pixel-based signal intensity, the net signal is obtained by subtracting a signal offset "$s_{offset}$" from the measured signal "$s_{measured}$". The signal offset may be automatically provided by the scanner device or may be empirically determined by identifying a minimal signal in the digital representation of the molecular array produced by scanning the molecular array and processing the scanned data. An estimate of the variance of the per-pixel counts within the area of a digital representation of a molecular array corresponding to a feature or feature background is obtained as follows:

$$S^2_{s_{net}} = \frac{1}{n-1} \sum_{i=1}^{n} (s_{net} - \bar{s}_{net})^2$$

$$\text{where } \bar{s}_{net} = \frac{1}{n} \sum_{i=1}^{n} s_{net},$$

S=standard deviation, and
n=the number of pixels within the feature or feature background Thus, the variance of pixel counts or pixel-based signal intensities within a feature or feature background can be straightforwardly calculated from the net signals obtained from the digital representation of the scanned image of a molecular array.

In order to determine whether the pixel counts or pixel-based signal intensities within a feature or feature background are sufficiently uniform, the calculated variance "$S^2_{s_{net}}$" needs to be compared to a threshold value to determine whether or not the calculated variance, "$S^2_{s_{net}}$" falls below the threshold value and therefore is acceptable. While current methods employ values measured from negative control features included within a molecular array, or depend on manual inspection of pixel count distributions, the present invention employs a calculated variance model to obtain the threshold value. In one embodiment of the present invention, the calculated variance model "$\sigma^2$" is a linear combination of three different, independent model variances:

$$\sigma^2 = \sigma^2_{labeling\ and\ feature\ synthesis} + \sigma^2_{counting} + \sigma^2_{noise}$$

The model variance "$\sigma^2_{labeling\ and\ feature\ synthesis}$" is the variance expected for non-uniformities associated with target-molecule labeling, feature synthesis, and other solution and surface and chemistry effects. The model variance "$\sigma^2_{counting}$" is the variance expected in scanning measurement, or counting, error. The model variance "$\sigma^2_{noise}$" is the expected variance due to electronic noise in the scanner, background-level signal noise produced by the glass substrate of the molecular array, and other such noise.

Figure 9A:
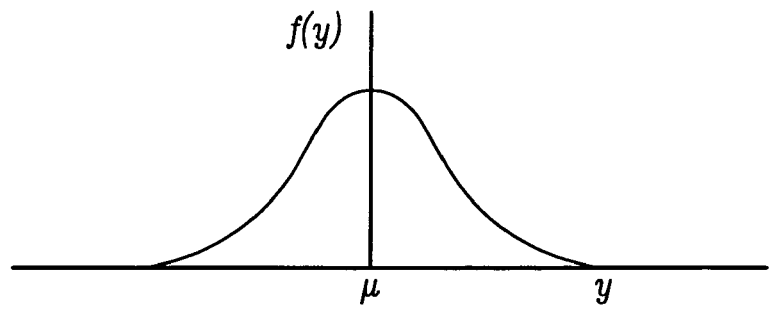
FIG. 9A shows a generalized normal distribution.

In one embodiment of the present invention, the non-uniformity associated with labeling and feature synthesis is considered to be normally distributed. FIG. 9A illustrates a generalized normal distribution, described by the following expression:

$$f(y) = \frac{e^{-(y-\mu)^2/2\sigma^2}}{\sigma\sqrt{2\Pi}}$$

where y=measured quantity,
μ=mean,
σ=standard deviation

Figure 9B:
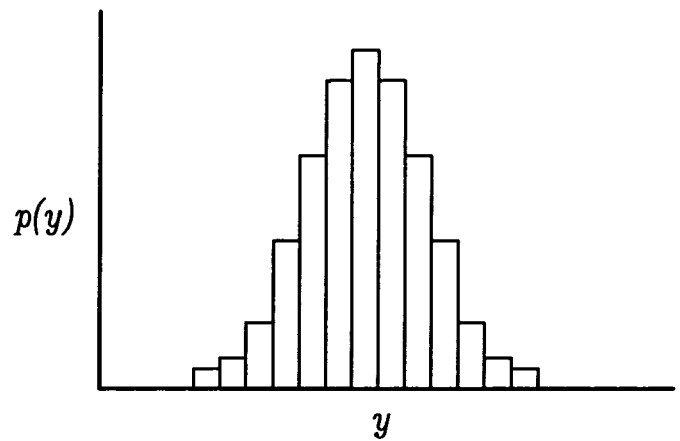
FIG. 9B shows a binomial distribution.

In the described embodiment of the present invention, the non-uniformity associated with scanner measurement error is considered to be distributed according to a Poisson distribution. FIG. 9B illustrates a binomial distribution, described by the following expression:

$$p(y) = \binom{n}{y} p^y q^{n-y}$$

where p(y)=probability of y positive outcomes,
p=probability of a positive outcome,
q=probability of a negative outcome, and
n=counts, time intervals, etc.

A Poisson distribution is the limit of the binomial distribution as n approaches infinity. The Poisson distribution is expressed as follows:

$$p(y) = \frac{\lambda^y}{y!} e^{-\lambda}$$

where $\lambda = \bar{y}$

The non-uniformity associated with electronic scanner noise and glass-substrate-background-level noise is considered to be a constant, in the described embodiment.

In the described embodiment, the model variance is "$\sigma^2$" is alternatively expressed as:

$$\sigma^2 = A\bar{s}^2_{net} + B\bar{s}_{net} + C$$

where $A\bar{s}^2_{net} = \sigma^2_{labeling\ and\ feature\ synthesis}$,
$B\bar{s}_{net} = \sigma^2_{counting}$,
$C = \sigma^2_{noise}$ The constant "A" can be estimated as the square of the coefficient of variation, $$\text{``}\frac{\sigma^2}{\bar{s}_{net}^2}\text{''},$$

which can be estimated based on analyzing large numbers of similar molecular arrays and computing the coefficient of variation in the analysis. In the case of in-situ arrays, a value of A=0.01 provides a good estimate for the square of the coefficient of variation due to labeling and feature synthesis non-uniformities.

For the scanner Poissonian noise, the signal to noise ratio is estimated, in the described embodiment, based on the number of molecules of chromophores and the number of photons produced by each molecule, as follows:

$$S/N = \sqrt{m}\sqrt{p}/\sqrt{p+1}$$

where m=number of chromophore molecules, and
p=number of photons/chromophore molecule Therefore, when the number of photons emitted per chromophore is large, the signal to noise expression is provided below:

$$S/N \approx \sqrt{m}$$

In the described embodiment, the scanner measures a signal of approximately 3.2 counts per chromophore molecule in a 10 micron by 10 micron pixel. Therefore, the number of chromophore molecules per pixel can be estimated by the mean counts per pixel $\bar{s}_{net}$ as follows:

$$m = \bar{s}_{net}/3.2$$

Thus, $$S/N = \sqrt{\bar{s}_{net}/3.2}$$
$$\sigma_{counting}^2 = (1/S/N)^2 = 3.2\bar{s}_{net}$$
$$B = 3.2$$

In the described embodiment, the constant "C" is found, through scanning experiments, to have a value of 144. The estimated values of constants "A," "B," and "C" obviously vary with varying experimental conditions, target and probe biopolymers, molecular array substrates, chromophores, and scanning and data reduction equipment.

Figure 9C:
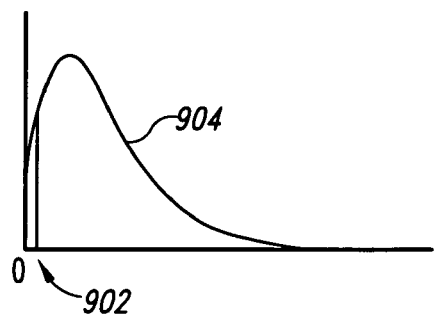
FIG. 9C shows a representative $\chi^2$ distribution.

Using the above-described variance model, a threshold value, or $\sigma_{max}^2$, can be estimated using an assumption that the following expression is distributed according to a $\chi^2$ distribution with n−1 degrees of freedom, where n is the number of feature or feature background pixels:

$$\frac{(n-1)\hat{\sigma}^2}{\sigma^2}$$

where $\sigma^2$ is the true feature or feature background variance under the assumption that the model is valid, and the feature or feature background is not an outlier A representative $\chi^2$ distribution is shown in FIG. 9C, where the $\chi^2$ distribution is expressed as follows:

$$f(y) = \begin{cases} \frac{y^{(v/2)-1}e^{-y/2}}{2^{v/2}\Gamma(v/2)}, & y \geq 0, v \geq 0 \\ 0 \end{cases}$$

where $\Gamma(v/2) = \int_0^\infty y^{(v/2)-1}e^{-y}dy$ v=number of degrees of freedom The threshold value is determined by selecting a lower bound "$\chi_x$" (902 in FIG. 9C) such that the probability that the $\chi^2$-distributed expression (n−1) $\hat{\sigma}^2/\sigma^2$ is greater than 1−α/2, where the probability 1−α/2 is the areas under the distribution curve 904 to the right of the lower bound "$\chi_x$" 902, according to the following expression:

$$p\left[\chi_x^2 \leq \frac{(n-1)\hat{\sigma}^2}{\sigma^2}\right] = 1 - \alpha/2$$

By rearranging the above expression, an equivalent expression is obtained:

$$p\left[\sigma^2 \leq \frac{(n-1)\hat{\sigma}^2}{\chi_x^2}\right] = 1 - \alpha/2$$

Thus:

$$\sigma_{max}^2 = \frac{(n-1)\hat{\sigma}^2}{\chi_x^2}$$

It should be noted that, although the above described variance model has been found to provide an effective basis for outlier detection, many other type of variance models are possible. Additional terms can be included, to account for other types of variances, terms may be modified, to more precisely describe the variances, and terms may be deleted from the above expression for the model variance. The techniques of the present invention may use any of the many possible model variances for outlier detection.

A C++-like pseudocode implementation showing an embodiment of the present invention is provided below. Note that the pseudocode implementation is not intended to describe a complete data processing program for molecular array data, but only to provide sufficient detail to illustrate one possible embodiment the above-described outlier identification methodology as the embodiment might occur within a molecular array data processing program, or in molecular array scanning and data processing equipment. The molecular array data processing program including the techniques of the present invention analyzes data scanned from a molecular array to produce experimental or diagnostic results which are stored in a computer-readable medium, transferred to an intercommunicating entity via electronic signals, printed in a human-readable format, or otherwise made available for further use.

First, the pseudocode implementation includes several constants and enumerations:

```
1  const int numColors=2;
2  enum color {RED, GREEN};
3  const int numAreas=2;
4  enum area {FEATURE, BACKGROUND};
```

The enumeration "color" contains a value for each different type signal, or scanning wavelength, and the number of different types of signals is provided by the constant "numColors." Similarly, areas that can be counted and analyzed statistically include features and feature backgrounds, described in the enumeration "area." The constant "numAreas" describes the number of areas in the enumeration "area." Thus, the pseudocode implementation includes analysis of both red and green signals for features as well as for feature backgrounds.

Next, the pseudocode implementation includes the class "scannedData," provided below:

```
1   class scannedData
2   {
3       private:
4           int* data;
5           int rowSize;
6           int* colSize;
7           int total;
8           bool outlying;
9
10      public:
11
12          int getRowSize( ) {return rowSize;};
13          int getColSize(int row) {return *(colSize + row);};
14          int getPixelCount(int row, int col);
15          int getTotal( );
16          void setTotal(int t) {total = t;};
17          bool getOutlying( ) {return outlying;};
18          void setOutlying(bool y) {outlying = y;};
19          scannedData(int* data);
20  };
```

An instance of the class "scannedData" describes the pixel-based signal intensities, or counts, for a particular background or feature area of a scanned molecular array. The pixels are assumed to be rectilinearly oriented, with the shape of the area having a major horizontal axis, or row, that intersects with all columns of pixels within the area. Thus, the pseudocode implementation can model square features, disk-shaped features, elliptically shaped features, and other similar symmetrical closed forms. The class "scannedData" contains the following data members: (1) "data," a pointer to the pixel counts; (2) "rowSize," the size, in columns, of the major horizontal axis, or major row; (3) "colSize," a pointer to the sizes of columns that include each pixel of the major row; (4) "total," a total number of counts for the area of the scanned image; and (5) "outlying," a Boolean value indicating whether or not the distribution of counts within the area is non-uniform. The class "scannedData" includes various member functions for setting and retrieving the values of the above-described data members, a member function "getPixelCount" that returns the per-pixel count measured by a scanning device by the pixel with row and column coordinates supplied as arguments, and a constructor "scannedData" that takes raw data as input. An implementation for the member function "getPixelCount" and the constructor are not provided, as the implementations are quite dependent on the format of the raw data and implementation of other portions of the data processing package, and are outside the scope of the present invention.

Next, the pseudocode implementation includes a declaration of the class "feature," provided below:

```
1   class feature
2   {
3       private:
4           int x_coordinate;
5           int y_coordinate;
6           scannedData *features;
7
8       public:
9           bool outlier(area a, color c)
10              {return features[a * numAreas + c].getOutlying( );};
11          int getCount(area a, color c)
12              {return features[a * numAreas + c].getTotal( );};
13          feature(scannedData* data, int* offsets,
14              float* A, float* B, float* C, float chiSquaredXPoint,
15              int x, int y);
16          virtual ~feature( );
17  };
```

An instance of the class "feature" describes a feature of the molecular array, and includes a pointer to an array of instances of the class "scannedData," described above, for the areas corresponding to the feature and to the background feature scanned at red and green visible wavelengths. The class feature includes the following data members: (1) "x_coordinate," the x coordinate of the feature in a rectilinear grid of features that comprises the molecular array; (2) the y coordinate of the feature; and (3) "features," a pointer to an array of instances of the class "scannedData." The class feature includes the following member functions: (1) "outlier," declared and implemented on lines 9 and 10, above, which returns a Boolean value indicating whether or not the area of the feature corresponding to argument "a" is an outlier with respect to the signal provided by argument "c;" (2) "getCount," declared and implemented above on lines 11–12, which returns the total net signal for either the background of the feature or the feature and scanned at a particular wavelength; and (3) "feature," a constructor for the feature.

The constructor for the class "feature" contains the code relevant to one embodiment of the present invention. An implementation for the constructor "feature" is provided below:

```
1   feature::feature(scannedData* data, int* offsets,
2       float* A, float* B, float* C, float chiSquaredXPoint,
3       int x, int y)
4   {
5       int total;
6       int total2;
7       int num;
8       int count;
9       double s_net;
10      double s_net2;
11      double s2_model;
12      double s2_max;
13      double s2;
14
15      features = data;
16      x_corrdinate = x;
17      y_coordinate = y;
18
19      for (int i = 0; i < numColors; i++)
20      {
21          for (int j = 0; j <= numAreas; j++)
22          {
23              total = 0;
```

```
-continued
24          total2 = 0;
24          num = 0;
25
26          for (int k = 0; k < data->getRowSize( ); k++)
27          {
28              for (int l = 0; l < data->getColSize(k); l++)
29              {
30                  count = data->getPixelCount(k, l) - *offsets;
31                  total2 += count * count;
32                  total += count;
33                  num++;
34              }
35          }
36          s_net = total/num;
37          s_net2 = s_net * s_net;
38          s2_model = (s_net2 * (*A)) + (s_net * (*B)) + *C;
39          s2_max = s2_model * (num - 1)/chiSquaredXPoint;
40          s2 = total2/num - s_net2;
41          if (s2 <= s2_max) data->setOutlying(false);
42          else data->setOutlying(true);
43          data->setTotal(total);
44          data++;
45          offsets++;
46          A++;
47          B++;
48          C++;
49      }
50  }
51 }
```

The constructor "feature" takes the following arguments: (1) "data," a pointer to an array of instances of the class "scannedData;" (2) "offsets," a pointer to an array of offsets, corresponding to the term "$s_{offset}$" in the above-described expression for the net signal "$s_{net}$"; (3) "A," "B," and "C," pointers to arrays of constants for each type of scanned in area, e.g., feature or feature background scanned in red or green light, where the constants in the arrays correspond to the constants "A," "B," and "C," in the above-described expression for the model variance "$\sigma^2$;" (4) "chiSquaredXPoint," the threshold variance value "$\chi^2_x$," described above; and (5) "x" and "y," the x and y coordinates for the feature. On lines 5–13, a number of local variables are declared. These local variables include: (1) "total," pixel counts obtained from an area associated with a feature during a particular scan; (2) "total2," the square of the total pixel counts; (3) "num," the number of pixels in the area; (4) "count," a particular net count for a pixel "$s_{net}$;" (5) "s_net," the average value of the net signals from an area; (7) "s_net2," the square of the average net signals from an area; (8) "s2_model," the calculated model variance for an area feature under a particular scan; (8) "s2_max," the threshold value "$\sigma^2_{max}$," described above; and (9) "s2," the estimated variance for the pixel intensities within the area. On lines 15–17, member data for the class feature are initialized based on the values of supplied arguments. In the nested for-loops of lines 19–50, each of the instances of the class "scannedData" describing scans of areas associated with the feature are processed according to the above-described technique for obtaining net signals and determining whether or not the uniformity of the signal intensities within an area are acceptable. Thus, the code of lines 22–48 is executed for each scan of each areas associated with the feature. In the case of the described embodiment, instances of the class "scannedData" represent red and green scans of the feature background and the feature. In the for-loop of lines 26–35, the square of the total net signals, the total net signals, and the number of pixels in an area are calculated for the area. On line 36, the value $s_{net}$ is calculated. On line 37, the value $s_{net}^2$ is calculated. On line 38, the value $\sigma^2$ is calculated. On line 39, the value $\sigma^2_{max}$ is calculated. On line 40, the estimated variance for the pixel counts within the area is calculated. On lines 41–42, the member data "outlier" for the instance of the class "scannedData" is set to "false" if the estimated variance is less than or equal to the threshold variance $\sigma^2_{max}$, and is set to "true" otherwise. On line 43, the member data "total" is set to the total net signal count for the area. Finally, on lines 44–48, array pointers are incremented for the next iteration of the nested for-loops.

Although the present invention has been described in terms of a particular embodiment, it is not intended that the invention be limited to this embodiment. Modifications within the spirit of the invention will be apparent to those skilled in the art. For example, an almost limitless number of different implementations of the outlier detection method of the present invention can be written in any of many different programming languages, embodied in firmware, embodied in hardware circuitry, or embodied in a combination of one or more of firmware, hardware, or software, for inclusion in molecular array data processing equipment employing a computational processing engine to execute software or firmware instructions encoding techniques of the present invention or including logic circuits that embody both a processing engine and instructions. Various different variance models can be employed, including models with additional model variance terms corresponding to observed errors, defects, and noises different from, in addition to, or in place of those used in the described embodiment. Use of statistical variance modeling for generating variance thresholds for outlier detection can be applied to many different types of molecular arrays, and to many other molecular-array-like scientific and diagnostic devices. In the described embodiment, the techniques of the present invention are employed to detect outlier features and features backgrounds, but the same techniques may be applied to identify non-uniformity in other regions of a scanned image of a molecular array. The techniques of the present invention may be applied to scanned images of molecular arrays, regardless of the wavelength of light used in an optical scan, energy levels of emitted radiation detected, or other type of signal detection employed to generate the scanned image. Of course, each different type of scanning device, molecular array, type of signal detected, and other variations will need a corresponding variance model for calculating useful variance thresholds.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

What is claimed is:

1. A method for identifying a non-uniform measured signal distribution in a region of a scanned image of a molecular array, the method comprising:
providing a variance model for measured signal distributions within regions of the molecular array;
determining a variance of measured signals within the region; and
determining whether or not the region contains a non-uniform measured signal distribution by comparing the determined variance of measured signals within the region to the variance model.

2. The method of claim 1 further including determining a variance threshold from the variance model, and wherein comparing the determined variance of measured signals within the region to the variance model comprises comparing the determined variance of measured signals within the region to the determined variance threshold.

3. The method of claim 2 wherein the scanned image comprises pixels, each pixel associated with a count representing a signal measured from a corresponding portion of the molecular array.

4. The method of claim 3 wherein the variance model is a linear combination of model variance terms.

5. The method of claim 4 wherein model variance terms include:
a variance term arising from non-uniformities associated with target-molecule labeling, feature synthesis, probe molecule application, and other solution and surface chemistry effects;
a variance term arising from non-uniformities associated with scanner counting errors; and
a variance term arising from non-uniformities associated with electronic noise in a scanner, background-level signal noise arising from a molecular array substrate, and other noise.

6. The method of claim 5 wherein non-uniformities associated with target-molecule labeling, feature synthesis, probe molecule application, and other solution and surface chemistry effects are assumed to be normally distributed, wherein non-uniformities associated with scanner counting errors are modeled by a Poisson distribution, and wherein non-uniformities associated with electronic noise in the scanner, background-level signal noise produced by the molecular array substrate, and other noise are assumed to produce a constant variance.

7. The method of claim 3 wherein the variance model is an expression including a mean pixel count for the region as a variable.

8. The method of claim 2 wherein calculating a variance threshold from the variance model further includes assuming a chi-squared distribution for one less than the number of pixels multiplied by the model variance and divided by the theoretical variance of measured signals within the region, and, based on the chi-squared distribution assumption, selecting a threshold variance value below which the determined variance of measured signals within the region has a high probability of indicating an acceptably uniform distribution of measured signals within the region.

9. The method of claim 1 wherein the region is selected from among a feature and a feature background.

10. The method of claim 1 wherein the variance model is provided according to chemical and physical properties of the molecular array, electronic and physical properties of a scanning device, and experimental conditions to which the molecular array is exposed.

11. A computer-readable medium having computer executable instructions stored thereon, for performing the method of claim 1.

12. A system for identifying a non-uniform measured signal distribution in a region of a scanned image of a molecular array, the system comprising:
a digital representation of the measured signals in the region of the scanned image of the molecular array stored within a memory component;
a variance model for measured signal distributions within regions of the molecular array stored within a memory component; and
a computational processing engine that calculates a variance of measured signals within the region and compares the calculated variance with the variance model to determine whether or not the region contains a non-uniform measured signal distribution by comparing the determined variance of measured signals within the region to the variance model.

13. The system of claim 12 wherein the variance model further includes a variance threshold to which the computational processing engine compares the calculated variance.

14. The system of claim 12 wherein the digital representation of the measured signals in the region of the scanned image of the molecular array comprises a number of pixels, each pixel associated with a count representing a signal measured from a corresponding portion of the molecular array.

15. The system of claim 12 wherein the variance model is a linear combination of model variance terms.

16. The system of claim 15 wherein model variance terms include:
a variance term arising from non-uniformities associated with target-molecule labeling, feature synthesis, probe molecule application, and other solution and surface chemistry effects;
a variance term arising from non-uniformities associated with scanner counting errors; and
a variance term arising from non-uniformities associated with electronic noise in a scanner, background-level signal noise arising from a molecular array substrate, and other noise.

17. The system of claim 16 wherein non-uniformities associated with target-molecule labeling, feature synthesis, probe molecule application, and other solution and surface chemistry effects are assumed to be normally distributed, wherein non-uniformities associated with scanner counting errors are modeled by a Poisson distribution, and wherein non-uniformities associated with electronic noise in the scanner, background-level signal noise produced by the molecular array substrate, and other noise are assumed to produce a constant variance.

18. The system of claim 12 wherein the variance model is an expression including a mean pixel count for the region as a variable.

19. The system of claim 12 wherein the variance model is based on chemical and physical properties of the molecular array, electronic and physical properties of a scanning device, and experimental conditions to which the molecular array is exposed.

* * * * *